US010922651B2

United States Patent
Langdon

(10) Patent No.: US 10,922,651 B2
(45) Date of Patent: Feb. 16, 2021

(54) SYSTEMS AND METHODS FOR IMPROVING MEDICAL ORDER ENTRY FOR HIGH VOLUME SITUATIONS

(75) Inventor: Robert W. Langdon, Dallas, TX (US)

(73) Assignee: T-System, Inc., Dallas, TX (US)

(*) Notice: Subject to any disclaimer, the term of this patent is extended or adjusted under 35 U.S.C. 154(b) by 816 days.

(21) Appl. No.: 12/171,160

(22) Filed: Jul. 10, 2008

(65) Prior Publication Data

US 2010/0010833 A1    Jan. 14, 2010

(51) Int. Cl.

| | |
|---|---|
| G06Q 10/10 | (2012.01) |
| G16H 40/20 | (2018.01) |
| G16H 80/00 | (2018.01) |
| G16H 10/60 | (2018.01) |
| G06Q 50/24 | (2012.01) |
| G06F 19/00 | (2018.01) |
| G16H 40/67 | (2018.01) |
| G16H 70/20 | (2018.01) |

(52) U.S. Cl.
CPC ............ *G06Q 10/10* (2013.01); *G06F 19/00* (2013.01); *G06Q 50/24* (2013.01); *G16H 10/60* (2018.01); *G16H 40/20* (2018.01); *G16H 80/00* (2018.01); *G06F 19/325* (2013.01); *G16H 40/67* (2018.01); *G16H 70/20* (2018.01)

(58) Field of Classification Search
CPC ........ G06Q 50/22; G06Q 50/24; G06Q 10/10; G06Q 10/06; G06Q 10/00; G06Q 20/204; G06Q 30/06; G06Q 40/02; G06Q 40/08; G06Q 10/08; G06F 19/32; G06F 19/34
See application file for complete search history.

(56) References Cited

U.S. PATENT DOCUMENTS

| 5,077,666 | A | * | 12/1991 | Brimm et al. ..................... 705/2 |
| 5,247,611 | A | * | 9/1993 | Norden-Paul et al. ........ 715/217 |
| 5,265,010 | A | * | 11/1993 | Evans-Paganelli et al. ................. 600/301 |
| 5,953,704 | A | * | 9/1999 | McIlroy et al. .................... 705/2 |
| 6,018,713 | A | * | 1/2000 | Coli ..................... G06F 19/322 705/2 |
| 2002/0046346 | A1 | * | 4/2002 | Evans ........................... 713/200 |
| 2002/0147614 | A1 | * | 10/2002 | Doerr et al. ...................... 705/2 |

(Continued)

OTHER PUBLICATIONS

Murff, Harvey J; Kannry, Joseph. "Physician Satisfaction With Two Order Entry Systems," Journal of the American Medical Informatics Association. Sep./Oct. 2001. vol. 8, Iss. 5; p. 499, 11 pgs.*

(Continued)

*Primary Examiner* — Rachel L. Porter
(74) *Attorney, Agent, or Firm* — Norton Rose Fulbright US LLP

(57) ABSTRACT

By arranging the input screen of a computerized medical order entry system to display pre-defined order-set possibilities for several categories (for example, labs, diagnostic, staff, medications) where the displayed order-set is directly related to a selected one of a plurality of medical emergency conditions, the physician can easily select orders from a single screen while conducting a patient interview or examination. The system allows the physician to concurrently select orders from order-sets associated with medical conditions different from the initially selected medical condition. In one embodiment, an elapsed time for an order is displayed for overall monitoring of patients.

14 Claims, 13 Drawing Sheets

(56) References Cited

U.S. PATENT DOCUMENTS

| | | | |
|---|---|---|---|
| 2003/0195771 A1* | 10/2003 | Fitzgerald et al. | 705/2 |
| 2004/0078231 A1* | 4/2004 | Wilkes et al. | 705/2 |
| 2004/0153341 A1* | 8/2004 | Brandt et al. | 705/2 |
| 2005/0015279 A1* | 1/2005 | Rucker | 705/2 |
| 2005/0209880 A1* | 9/2005 | Drelicharz et al. | 705/2 |
| 2006/0080620 A1* | 4/2006 | Dvorak et al. | 715/781 |
| 2006/0143041 A1* | 6/2006 | Tipirneni | 705/2 |
| 2006/0200369 A1* | 9/2006 | Batch et al. | 705/3 |
| 2007/0100660 A1* | 5/2007 | Carosso et al. | 705/2 |
| 2008/0164998 A1* | 7/2008 | Scherpbier et al. | 340/539.13 |

OTHER PUBLICATIONS

Baron, J. M., & Dighe, A. S.Computerized provider order entry in the clinical laboratory. Aug. 2011, Journal of pathology informatics, 2, 35. (Year: 2011).*

International Search Report and the Written Opinion issued for PCT/US2009/050108, dated Aug. 14, 2009, 7 pages.

\* cited by examiner

| | | |
|---|---|---|
| 21 — ☐ | Portable CXR - AP | 201 |
| 22 — ☐ | CXR - PA & Lat | 30 |
| 23 — ☐ | Abdomen/Acute Series | 202 |
| 24 — ☐ | Chest AP & Lat 2V | 203 |
| 25 — ☐ | CT Head w/o Contrast | 204 |
| 26 — ☐ | ... | |

CXR PA & Lat

| Reason for Study | Pregnancy |
|---|---|
| Pain | Yes |
| Fever | No |
| Contusion | Unknown |
| | |
| | Transport |
| | Wheelchair |
| | Stretcher |
| | Ambulatory |

☐ CT Abdomen
☐ CT Chest
☐ CT Head

60

| PATIENT | ORDER | TIME |
|---|---|---|
| 703-3 | H U M | 15 |
| X | H X U M | 45 |
| Y | | |
FIG. 8
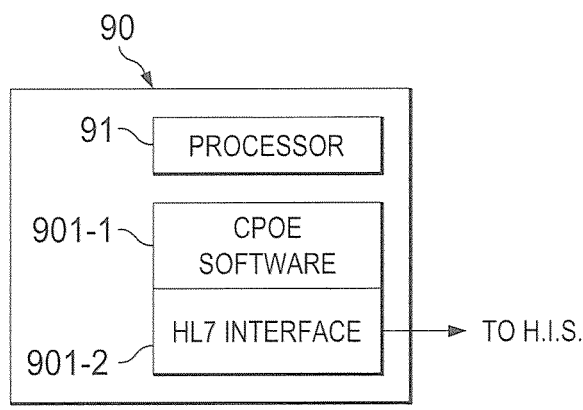
FIG 9A
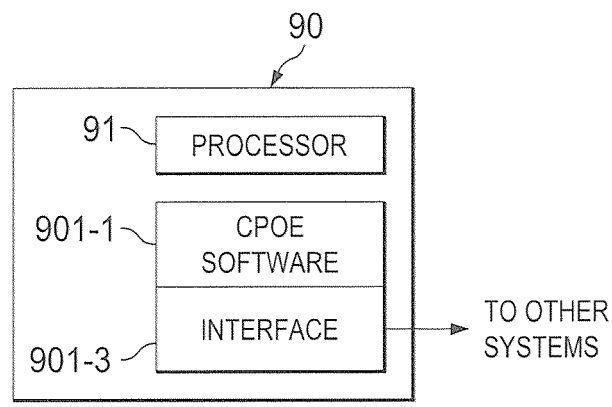
FIG. 9B

SYSTEMS AND METHODS FOR IMPROVING MEDICAL ORDER ENTRY FOR HIGH VOLUME SITUATIONS

TECHNICAL FIELD

This disclosure relates to hospital order entry systems and more particularly to systems and methods for improving medical order entry for high volume situations.

BACKGROUND OF THE INVENTION

Every hospital emergency department requires a system that allows a physician to place orders and communicate them to others, such as nurses, laboratories radiology, etc., in order for the patient to receive the necessary treatment. An order might be for intravenous or medication to be administered to the patient by a nurse. Another order might be for a laboratory test, for example a CBC or chemistry analysis of the blood. Such tests require blood to be drawn and delivered to (or picked up by) the laboratory. An order might be for a radiologic test(s), such as an x-ray, an MRI, CT scan, that must be performed in the radiology department and which requires the patient be transported to the radiology department.

The order might be a consultation whereby a request is made for a social worker to meet with the patient. Another order might require that a secretary phone a consulting psychiatrist to set up a visit with the patient, or that the secretary set up a cardiologist examination.

The important point being that the medical care giver needs to communicate with (provide orders for) a myriad of different services, some of which require logistical support and coordination from diverse departments. This is particularly true for high volume situations where a care giver is attending to multiple patients within minutes of each other.

Orders can be delivered in various ways all requiring cooperation between different departments to execute the orders properly. In critical care situations, the proper and timely distribution of orders and the proper and timely execution of the orders by the various hospital departments is vital to the welfare of the injured and sick patients. Proper and timely distribution of orders becomes especially important as the volume of patients increases. Compounding the problem is the fact that there are multiple details that must be specified for a given order.

While there are electronic order entry systems currently available, the most common remains a paper order entry system whereby the doctor handwrites the various orders on a piece of paper, and hands the paper to the nurse. The paper then can have on it perhaps up to 20 different orders destined to be carried out be several diverse and physically separated departments. The paper is typically handed to a secretary who then in some cases produces separate orders for each entity that must perform some task. In other situations, the secretary inputs the orders into a computer which then distributes the orders to the various departments. In some systems, the physician actually goes to a terminal and enters the orders him/herself.

For example, the secretary may fill out a form for radiology listing all of the items that radiology will need to know in order to perform the tasks ordered by the physician. Since each department has its own sets of requirements for receiving an order there are multiple manual steps that must be achieved in order for the patient to be properly served. A major problem with the paper order system is that it consumes a lot of resources. Nothing is automated in the workflow, so there is inefficiency and a resultant high consumption of time. Paper systems inherently lend themselves to delay in treatment involved with the multiple steps for every order. In an emergent situation, the paper system translates to potential patient safety issues as well as a high probability for error.

There are other order entry systems that rely on use of a computer system. These systems require a physician to navigate multiple screens in order to enter orders. In addition, existing computerized order entry systems require complex dialog sequences that are confusing for the users time consuming and prone to error. Fundamentally, the existing computerized systems are difficult to use and cannot be used at the bedside in real time. Thus, the physician must first interview and examine the patient and then walk to the computerized terminal before any of the data can be entered or the orders generated. Anything can happen in the intervening period between the examination and the entry of the desired information. For example, the physician can get called away to another emergency. Or he/she can forget items because of mind drift or distraction.

Even if the input terminals for the existing order entry systems were to be located bedside, their method of operation is so cumbersome as to make real time interaction (i.e. concurrent interaction with both the patient and the input device) not impractical.

BRIEF SUMMARY OF THE INVENTION

By arranging the input screen of a computerized medical order entry system to display pre-defined order-set possibilities for several categories (for example, labs, diagnostic, staff, medications) where the displayed order-set is directly related to a selected one of a plurality of medical emergency conditions, the physician can easily select orders from a single screen while conducting a patient interview or examination. The system allows the physician to concurrently select orders from order-sets associated with medical conditions different from the initially selected medical condition. In one embodiment, an elapsed time for an order is displayed for overall monitoring of patients.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

Figure 1A:
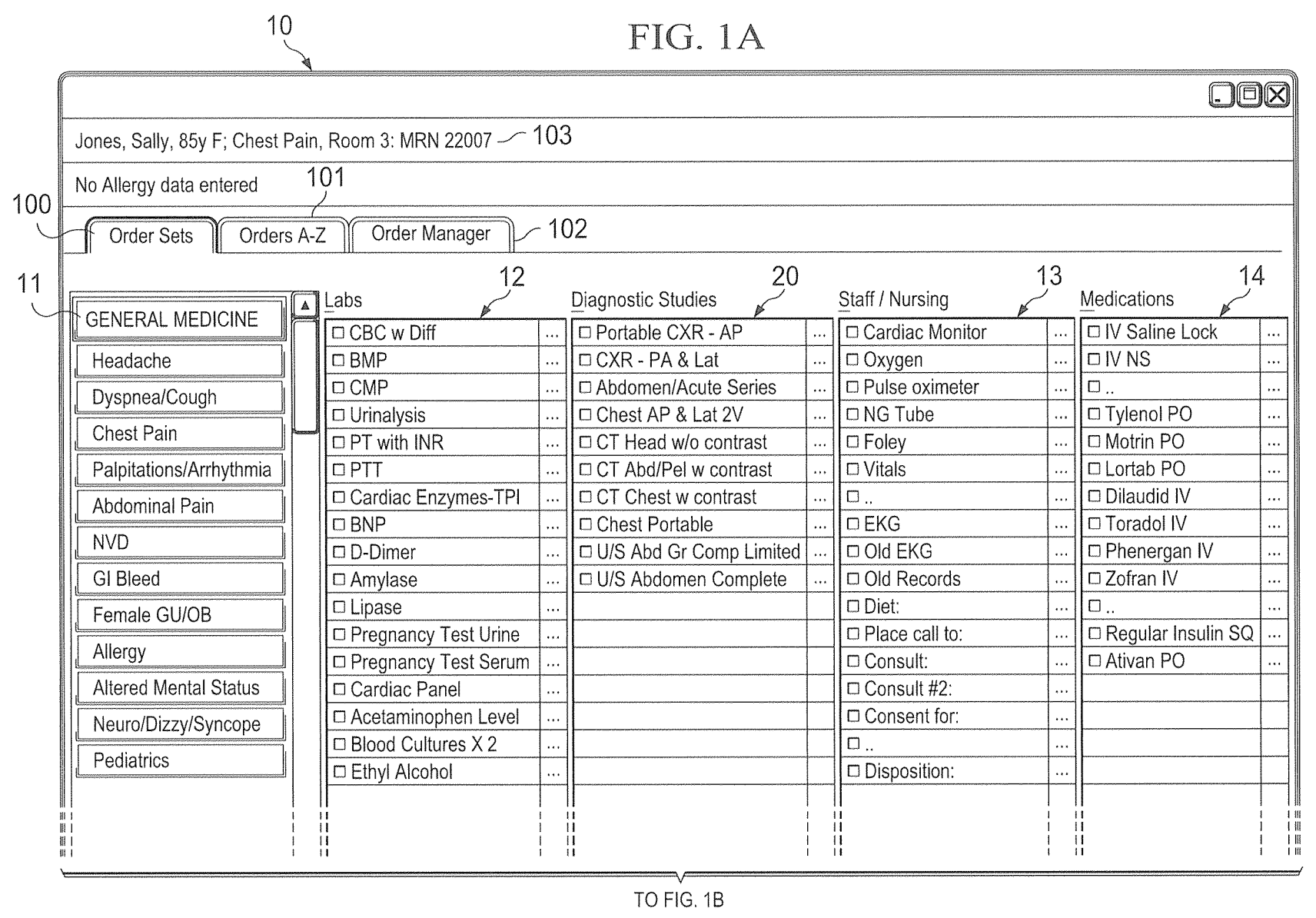
Figure 1B:
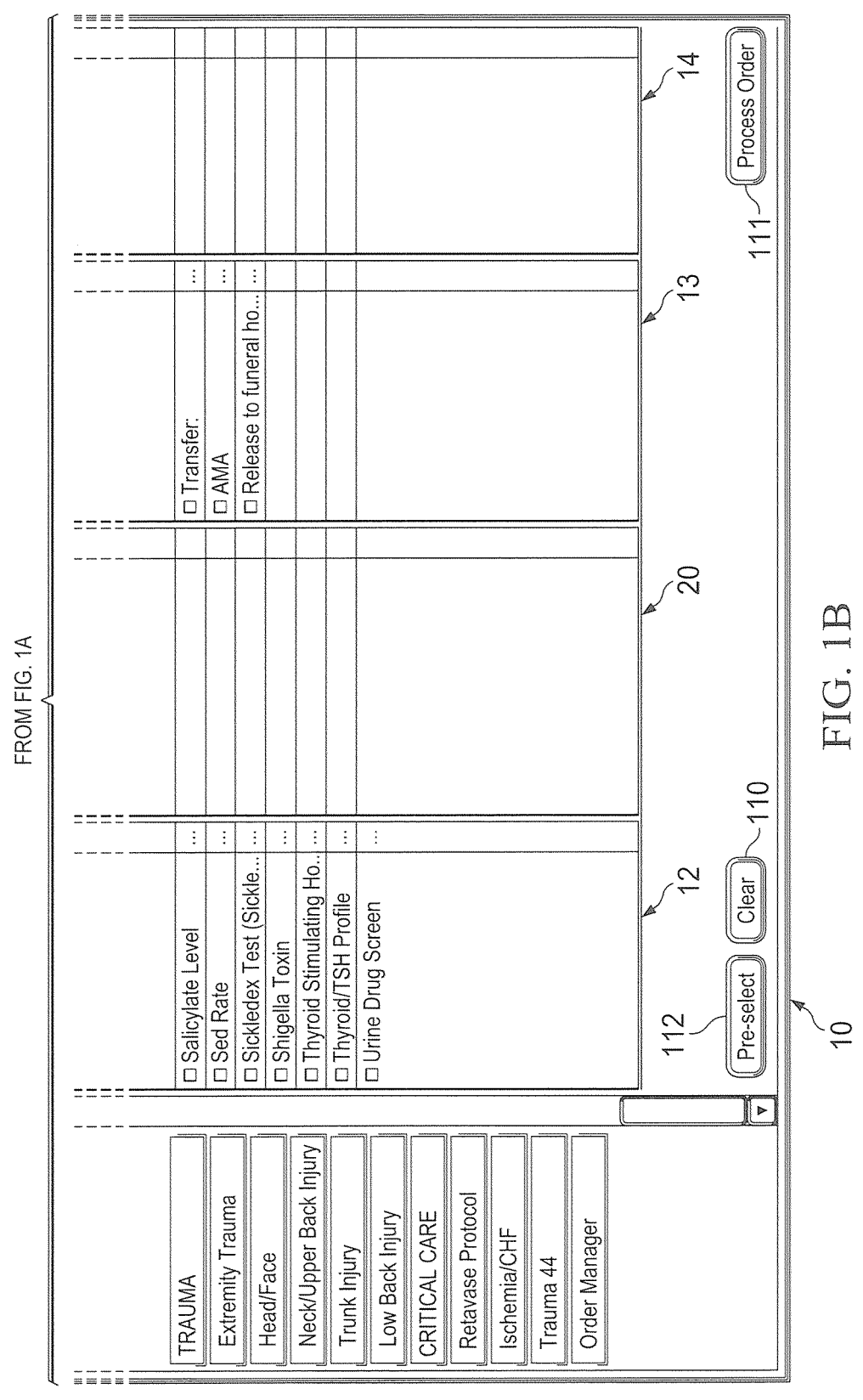

FIGS. 1A, 1B, 1C and 1D illustrate one embodiment of screen-shots of different order-sets;

FIG. 2 shows an expanded screen-shot of a portion of the listed order-sets;

FIG. 3 shows an expansion of a selected portion from a listed order;

FIGS. 5 and 6 show another view of order possibilities being presented to a physician;

FIG. 8 shows one embodiment 80 of a display for use in the emergency room;

FIGS. 9A and 9B show embodiments of a system for controlling the order entry procedure discussed herein;

DETAILED DESCRIPTION OF THE INVENTION

Figure 1C:
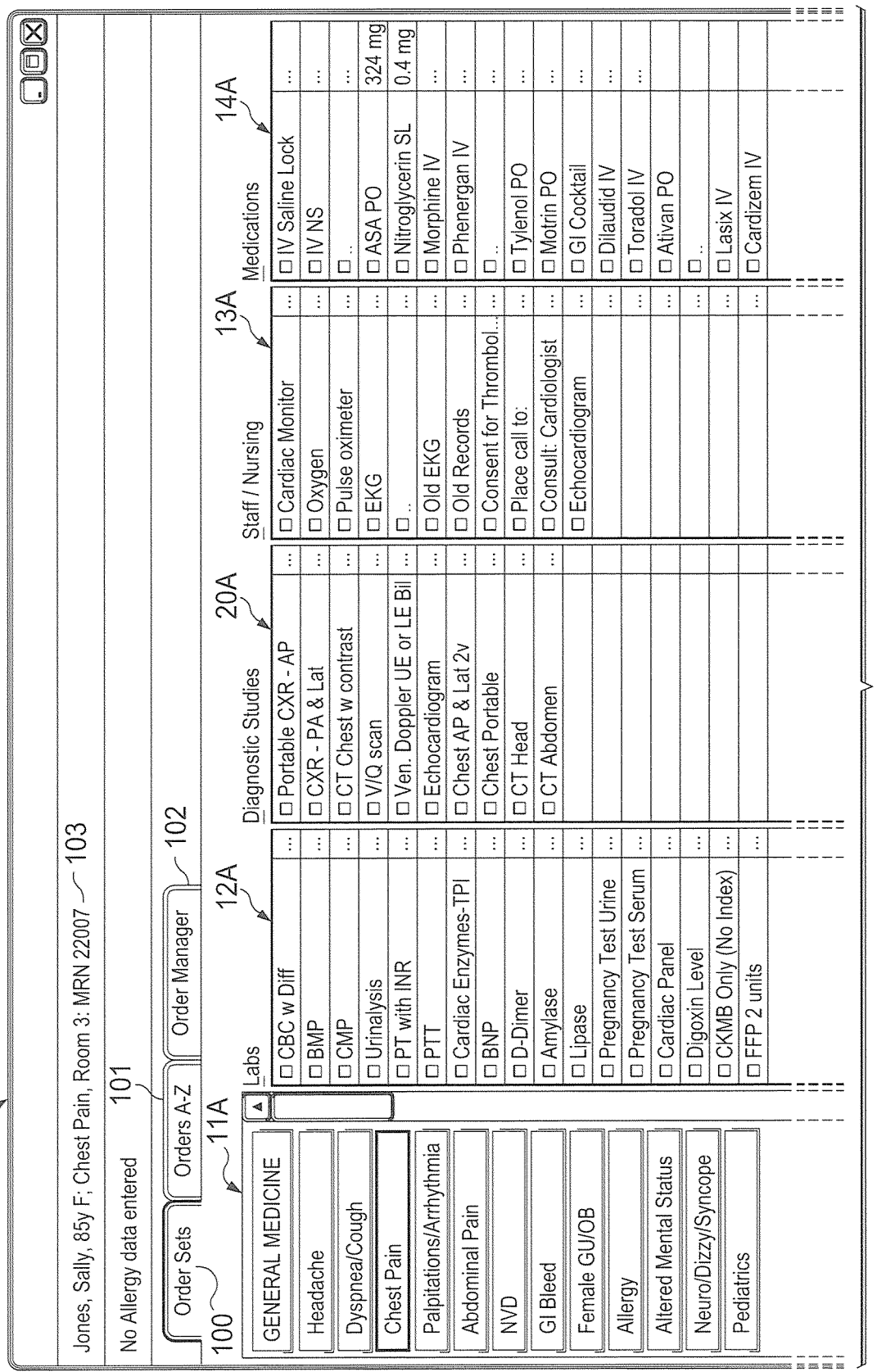

To begin with, an order-set for purposes of discussion herein is defined as a set of likely orders based on a problem or on a chief complaint of a patient. Prior systems also defined order-sets in the same manner, but they required the physician to work with a single order-set at a time. Thus, in such systems the physician must first place all the orders desired for a single "ailment" before being able to select orders that were pre-defined to be with different ailments. Since many patients present with more than one major "ailment" the "single order-set at a time" systems are cumbersome.

Since, as discussed above, it is desired to use the order system in real time while the physician is interacting with the patient, it is necessary that the physician be able to easily select the desired orders and to not be confined to the selection of orders in sequential fashion across multiple medical conditions. As will be discussed, the order entry system of this invention could be used from a laptop, a handheld device, or even a PC on a counter in the examination room. One aspect of the system is that the physician can simultaneously take the history, perform a physical exam, maintain a dialog with the patient and interact with the system to enter desired orders concurrently.

FIGS. 1A and 1B taken together illustrate one embodiment of screen-shot 10 showing four categories of orders. These are, labs 12, diagnostic studies 20, staff/nursing 13 and medications 14. Column 11 shows the various pre-defined "ailments" or medical conditions a patient, such as patient Sally Jones, may present with. As can be seen from line 103, Sally Jones is an 85 year old female who is presenting with chest pain, at least as a primary medical condition.

Figure 1D:
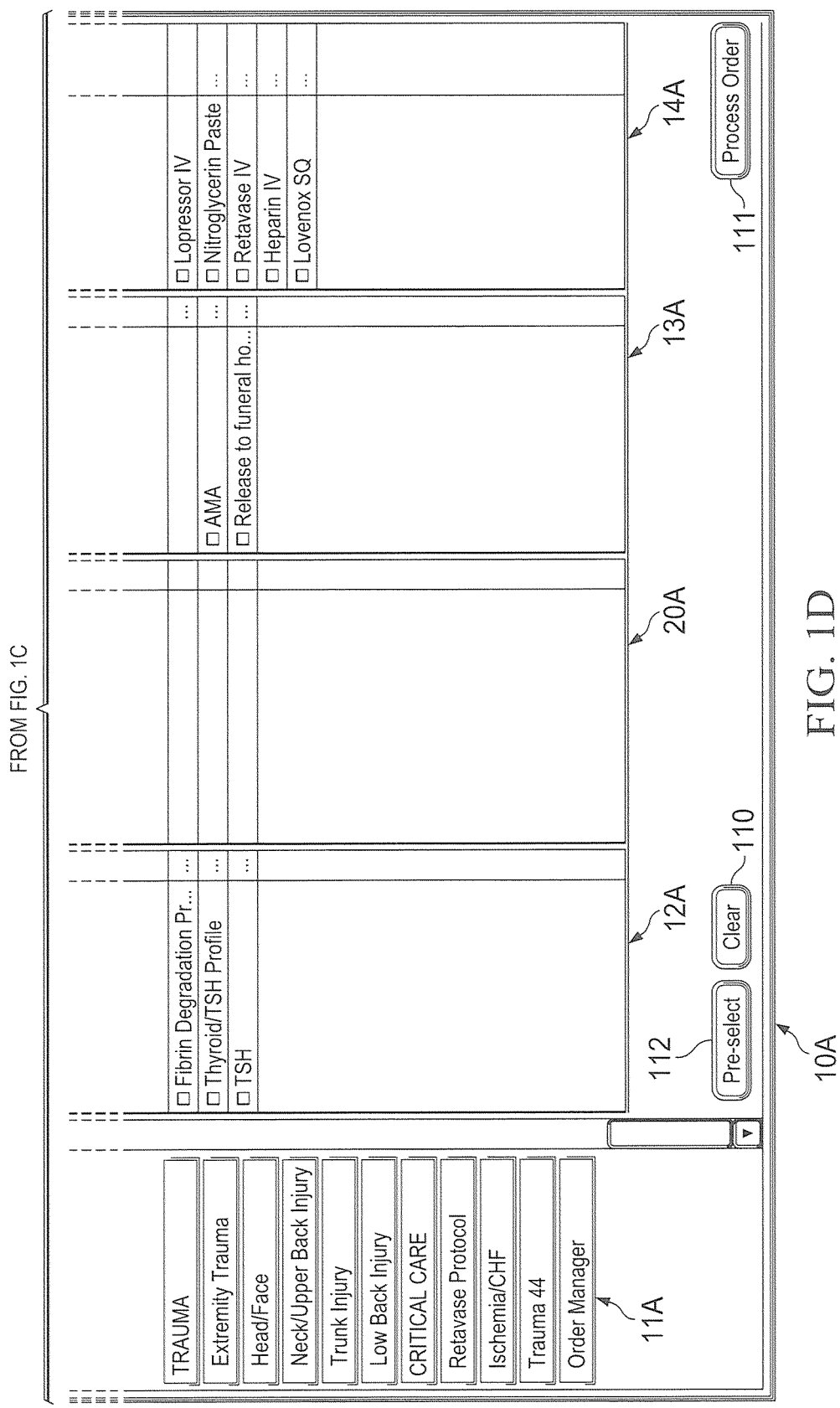

The physician, by selecting order sets 100 (a soft button if desired) is presented with screen 10 as shown. Screen 10 shows the default ailment "General Medicine" selected. This is a very generic set of orders. Any patient is likely to require some orders from this order set. Each of the other ailment's order sets approximate a tailored and optimized set of orders arranged for the particular ailment in question. The optimization is only approximate, because certain common orders are kept in consistent positions within a given column for the sake of consistency. For example, the "Chest Pain" ailment might optimally place the "Cardiac Enzymes" and "Cardiac Panel" orders at the top of the order set column. However, because the "CBC w Diff" and "BMP" procedures are common to this and many other ailments, they retain a consistent position at the top of the order set column. The physician then selects (again by soft button) item "Chest Pain" from column 11. Upon the selection of "Chest Pain" a pre-defined set of orders populates display 10A as is shown in FIGS. 1C and 1D taken together. Note that the specific possible orders of columns 12A, 20A, 13A, and 14A have changed from display 10 and now reflect the order-set appropriate for patients who present with chest pain. For instance, a chest pain patient may require Digoxin Level or Creatine Kinase MB ("CKMB") in addition to routine tests such as CBC w Diff and CMP. Under Diagnostic Studies, Chest Portable would display because that is one of the diagnostic tests that would typically be ordered for a patient with chest pain. Other diagnostic tests might be Chest AP & Lat 2V, CT scan of the head, or CT scan of the abdomen. They all would be displayed because they are the most common tests ordered for a chest pain patient. Nursing orders might be Consult Cardiologist, Echocardiogram, Consent for Thrombolytic Therapy, and for medication an order might be for Nitroglycerin Drip, Lasix IV, or other cardiac medications.

FIG. 2 shows an expanded screen-shot of column 20 of the listed order-sets and illustrates that each possible diagnostics order contained within the selected "General Medicine" medical condition (FIG. 1A) has a selection button, such as buttons 21-26. The orders can also have an expansion section, such as expansion section 201, 30, 202, 203, 204.

FIG. 3 shows an expansion 30 of the order Chest X-ray (CXR) from FIG. 2. As shown, the expansion file can ask questions relevant to the order, such as questions 302 and 303 and provides an area, such as area 301. Area 301 is for the physician to select a reason explaining to payers (insurance companies or Medicate/Medicaid) why they should pay for this Chest X-ray. The physician must write a reason acceptable to the payer or else the procedure's cost will not be reimbursed. It may be mandatory that the user complete one or more of these boxes because the receiving system may have required fields, such as pregnancy, etc. Transport mode is important so that the diagnostic department knows whether or not to send a wheel chair and/or an attendant. In some systems, the receiving department must have certain information or its own system will not function to accept the received order. Thus, it is important that all necessary information be entered initially and, in one embodiment, the system is designed to not allow the physician to place an order that is missing a required field.

Assume that the physician, while examining the patient, decides on a set of orders, he/she checks or touches the desired order and the selected order is then stored for future execution. If during the course of the examination the physician determines that other medical conditions need to be explored then the physician would select one or more additional medical conditions.

For example, assume the patient says to the physician, "My chest is hurting now, but yesterday I noticed blood in my stool." The physician then could select the pre-defined medical condition "GI Bleed" and a pre-established order-set appropriate to GI problems would appear on the display. The physician would select one or more orders from the GI Bleed order-set and then return to either the chest pain order-set or select a new medical condition.

Note that the particular orders in an order set can be established on a location by location basis and can be changed as desired. Each hospital site is free to create its own chief complaints, and each site is free to configure the components of each chief complaint. Also note that in the embodiment shown the buttons on the left (medical conditions) are always visible. The remaining four column headings (Labs, Diagnostic, Staff and Medication) to the right are also always visible, however the contents within each of the four columns changes depending on which medical condition button is selected. When the orders are ready to be transmitted the physician presses button 111, FIG. 1B to process all of the selected orders. Pre-select button 112 is used when the physician wants to select orders from an expanded set of order the hospital has determined are most frequently ordered for the patients with the selected medical condition. The system also loads the expansion section of pre-selected orders with default values designated by the hospital; however, it will not overwrite or replace any expansion information previously entered by the physician. The physician may continue to select/unselect orders and to change/enter expansion information after using button 112. Button 110 is used when the physician wants to undo the effect of button 112, however, it does not clear any selections entered manually by the physician button 112 also clears any default expansion information added when button 110 is used; however, it does not clear any expansion information manually entered by the physician.

Figure 4:
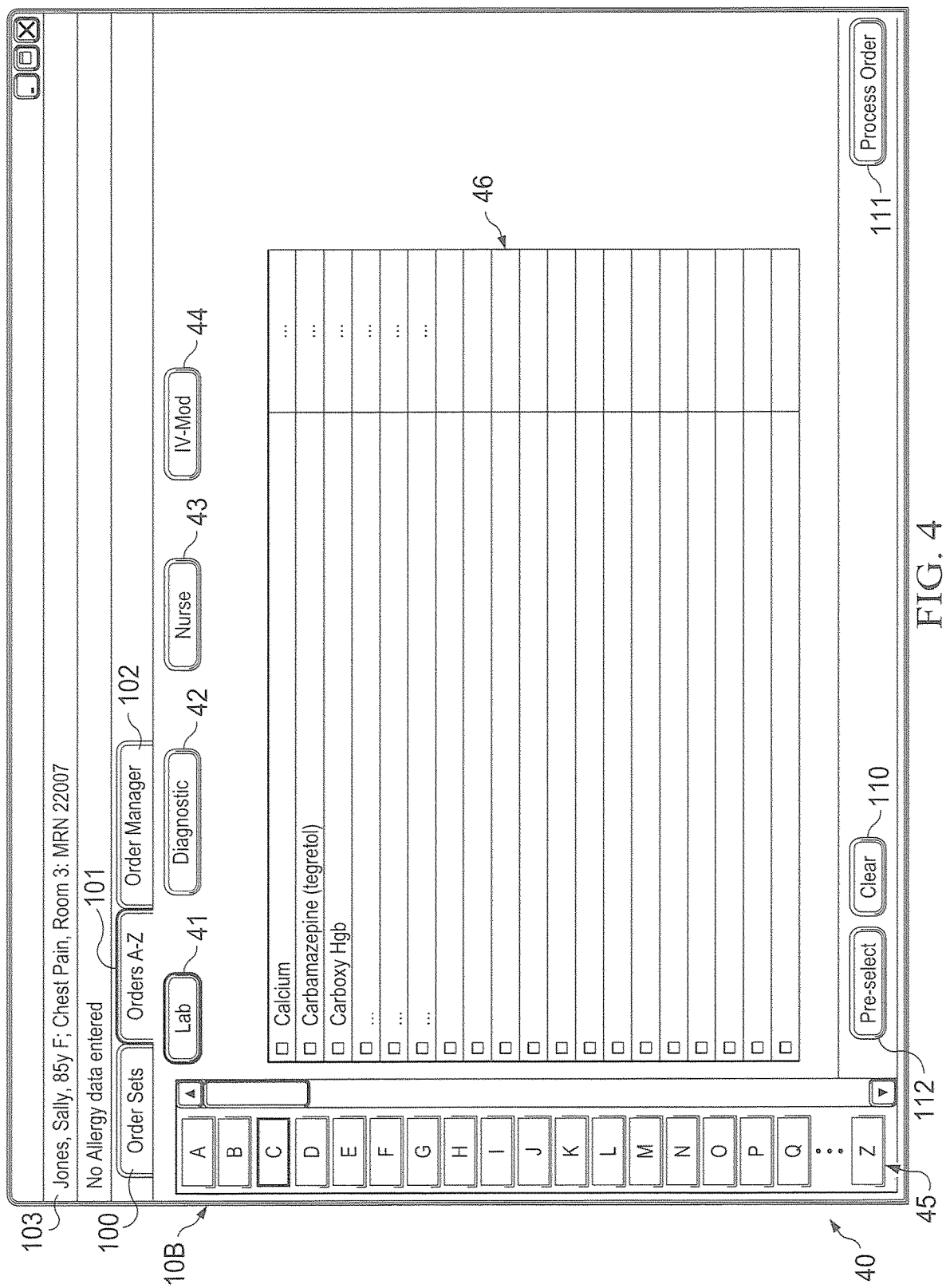
FIG. 4 shows one alternate presentation of order possibilities to a physician.

FIG. 4 shows one alternate presentation of order possibilities to a physician. When A to Z tab 101 is selected the user can search the entire library of possible orders. The user selects the order type from buttons 41-44 and then types in the first few letters of the desired order (on a pop-up keyboard or the like) and the available order possibilities populate the screen. For example, if the user selected lab 41 and then typed in C in column 45 the Calcium, Carbamazepine (tegretol), Carboxy Hgb . . . orders would be displayed.

Figure 5:
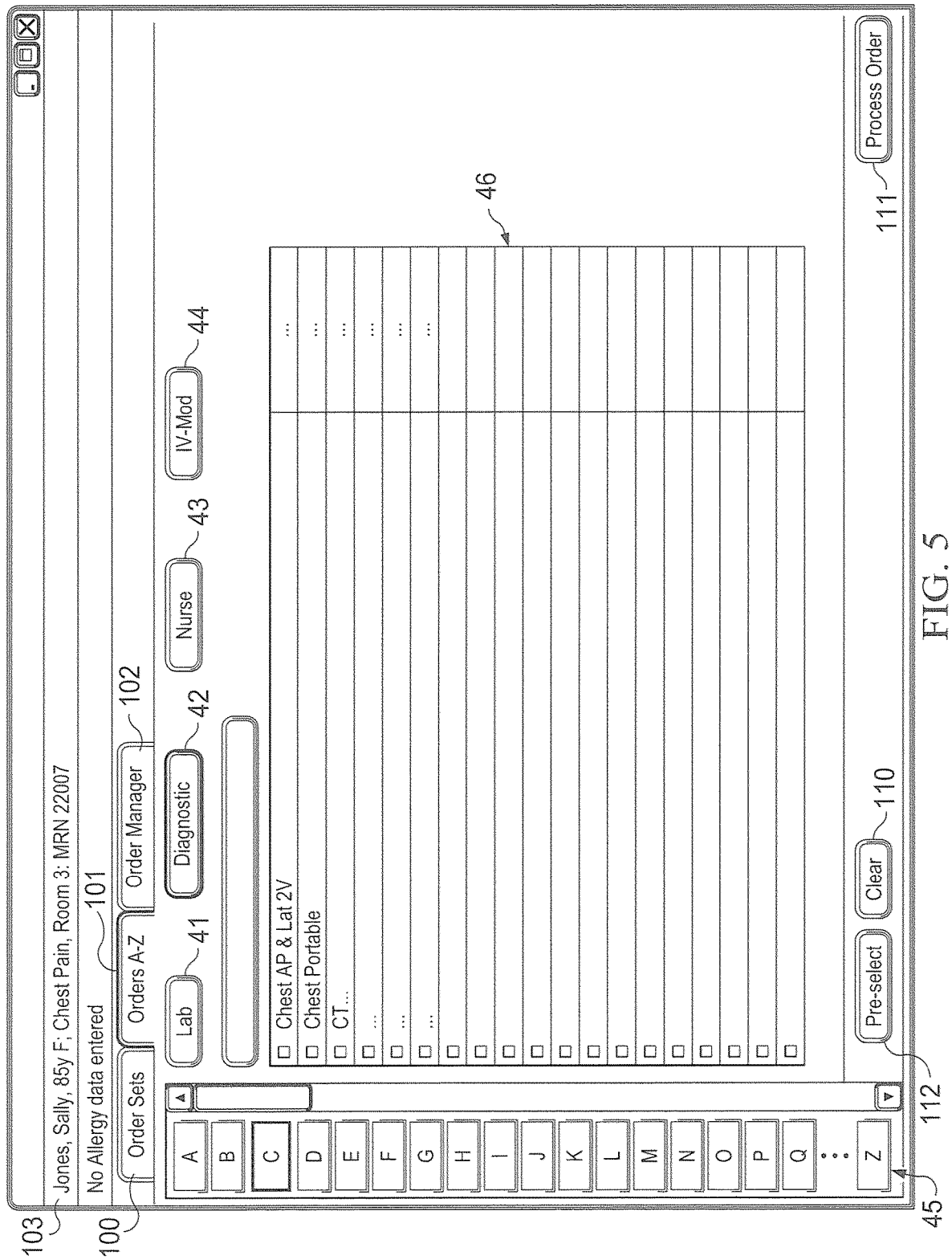

If the user had selected diagnostic 42, as shown in FIG. 5, then the possible diagnostic orders beginning with C would be displayed as shown. If the user selects CT then, as shown in screen display 60, FIG. 6 (shown on the same sheet as FIGS. 2 and 3), different possible CT scans would be displayed. Certainly, displays from FIGS. 5 and 6 could be combined as desired.

Figure 7:
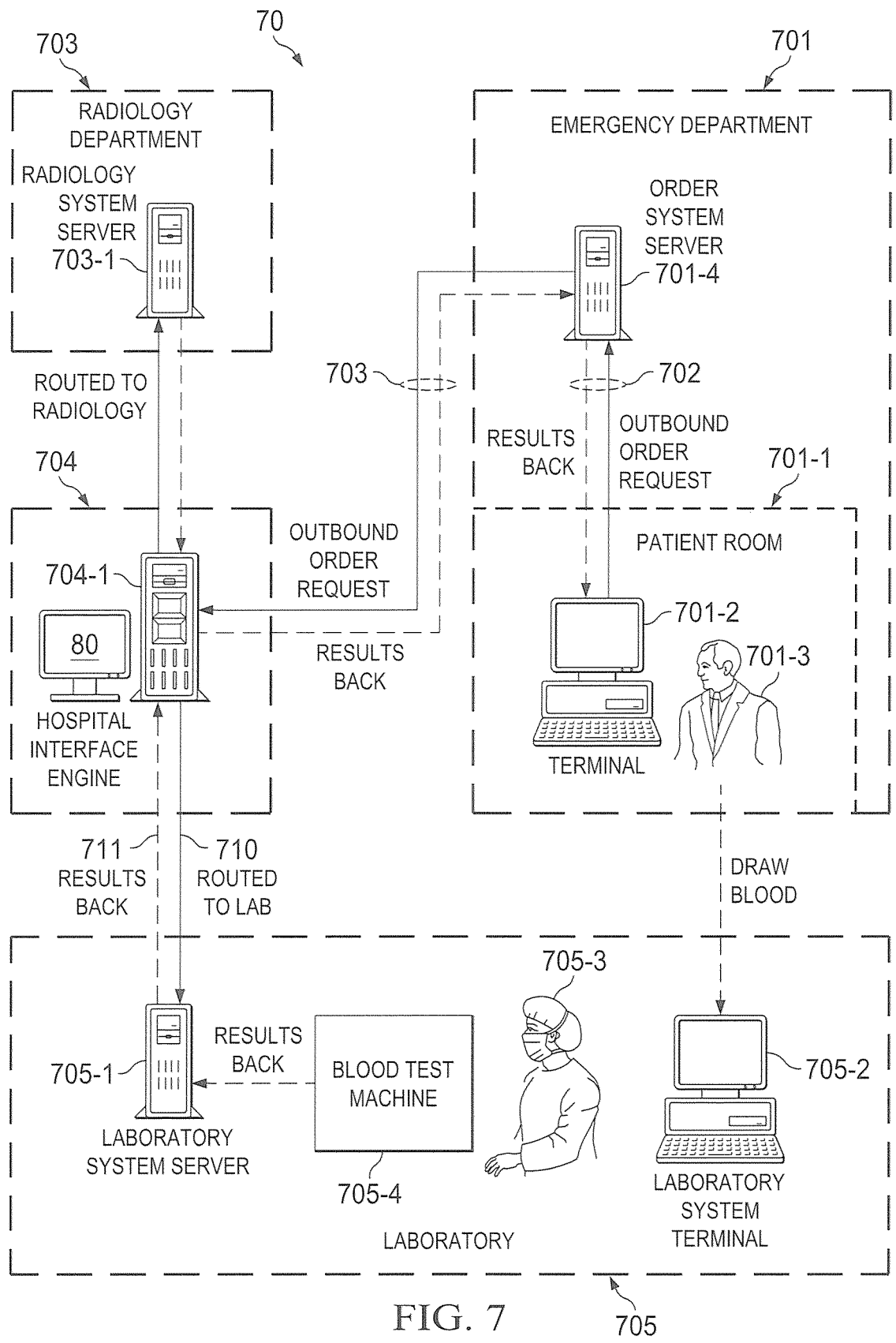
FIG. 7 illustrates a typical work flow in a hospital based upon orders placed by a physician.

FIG. 7 illustrates a typical work flow 70 in a hospital based upon orders placed by a physician. FIG. 7 shows three different departments in the hospital, namely, emergency department 701, laboratory 705 and radiology department 703. There are two types of workflow that typically occur. One is the workflow of what people are doing to provide care for the patient. The other one is the information flow between data processing systems.

In operation, patient room 701-1 has order entry terminal 701-2. Note that if desired this terminal can be anywhere, but preferably the terminal would be near the patient or a hand-held unit carried by the physician. The terminal, as well as the system, would be equipped with adequate security so that only a properly authorized attending physician (or other care giver) for a particular patient, such as patient 701-3, could log on and issue orders for that particular patient. This could be, for example, by a match between the physician (care giver) ID and the patient ID as controlled by a central operator or admittance procedure.

Link 702, which could be wireline or wireless, connects each input terminal to the order system server 701-4, which, in one embodiment, uses a Health Level 7 (HL7) system that passes messages around the hospital. Link 703 is used to transmit a message, for example a HL7 message in well-known format that contains the orders from the order system. The HL7 protocol is used in hospitals for communication of orders between departments and the system of the present invention could use that protocol or any other protocol. The hospital information system, upon receipt of a valid order(s) issues the necessary instructions, or provides the necessary information, to the proper department(s) so as to carry out the order(s).

Order system 701-4 maintains a database with a collection of entries for each patient. Some of the data stored for each patient would be a list of all orders that have been placed for the patient. The current workflow status from a series of work low fields can maintain when an order has been placed, acknowledged, completed, canceled, etc. System 701-4 maintains details of the order, such as what medication is prescribed, how many milligrams, what part of the body is being x-rayed, that kind of information. There would be an entry for every order. The database or application server also contains a database configured unique to the hospital which allows the software to map a given order, such as take a KUB x-ray, into whatever the code is that would have to be transmitted to the radiology department for the radiology department system.

For example, assume the order was for blood to be drawn for a specific set of tests. In such a situation, the central hospital system, in one embodiment, transmits an HL7 outbound order request (or redirects the incoming request) to the to laboratory system 705 via link 710. Upon receipt of the blood draw request for patient X, laboratory system server 705-1 would begin a workflow in the laboratory. For instance, screen 705-2 central to the laboratory or local to a specific phlebotomist, such as phlebotomist 705-3 (or both) would display or print out an instruction to draw blood from patient 701-3. When the blood is drawn it is taken to a blood test machine and the results are recorded in the computer associated with the testing. As results of the test become available they may be posted or, preferably, transmitted from the lab system server via link 711 to the hospital system's HL7 network and then to the appropriate care givers in the emergency facility.

The same type of procedure would apply to other orders, such as a radiology order which would be routed via link 712 to radiology department 703. In this case it is most likely that the patient would be delivered physically to the department for one or more scans or X-rays. This would be controlled, in part, by server 703-1 which would coordinate dispatching someone to bring the patient for testing.

The above discussion centered around a single control point, namely central point 704, controlling the workflow. That is only one possible workflow in a hospital. It may that in a given hospital when the doctor orders the test, that a nurse or someone in the ED is responsible for collecting the samples, and then through some other mechanism those samples get to the lab. The exact work flow is not critical. What is important is that the physician can rapidly and easily place orders in the system and that the system provides a tracking mechanism so that orders are completed in the proper sequence and in a timely manner. The order entry system requires the physician to enter the presence or absence of possible contraindications to a procedure and then sends the information to the appropriate department.

As shown in FIG. 7, when an order is entered into hospital system 704 an emergency room status display, such as display 80, is updated to display the order by patient ID. Then any further progress of each order is displayed. Thus, when blood is drawn for patient 701-3 that fact can be noted together with the time, if desired. Time limits for each order, or portions of each order, can be preset and the system then can set off alarms when a time limit is exceeded. These alarms can be colors, noise, electronic messages, or a combination thereof.

FIG. 8 shows one embodiment 80 of a display for use in the emergency room. Display 80 shows at least two columns 801 and 802 for each patient, such as for patient 701-3. The first column 801 shows an indicator of the type (usually by letter) of order that is outstanding. For example, L could be for lab, X meaning Radiology, E for EKG, etc. Color could be used to show status, new, in progress, completed, etc. The second column 802 shows a time clock, meaning if there are new orders, there is a small number, a two-digit number that shows how many minutes have elapsed since the oldest order was placed for that patient. So if a doctor places an order for Tylenol at 3:00, at 3:15 there is a number that says 15 because 15 minutes have elapsed. Column 802 allows everyone in the department, doctors, nurses, nurse managers, lab technicians, etc. to look at this airport view and quickly scan down column 802 looking for big numbers. If a big number is shown, such as 45 for patient X, that means that an order has not been processed for 45 minutes. Note that the time could be displayed for the oldest order for a patient, or order by order, or the time can be restarted when a new order is received.

FIG. 9A shows one embodiment 90 of a system for controlling the order entry procedure discussed herein. Software 901-1 running on processor 91 uses HL7 interface 901-2 to communicate with the other hospital (HIS) systems via the hospital's HL7 engine as discussed above. Other interfaces, such as interface 901-3 in FIG. 9B, can be used to interface with other systems, such as, for example, the display in the emergency room. If desired, the system can be arranged to facilitate sequential processing of orders to as to avoid interference between procedures. For example, the patient pick-up for transportation to the radiology department could be scheduled to occur after the phlebotomist draws blood. This feature can be accomplished, for example, by timing of the transmission of the order to the responsible department, or by setting a time for the performance of the order or by any other method desired.

Figure 10:
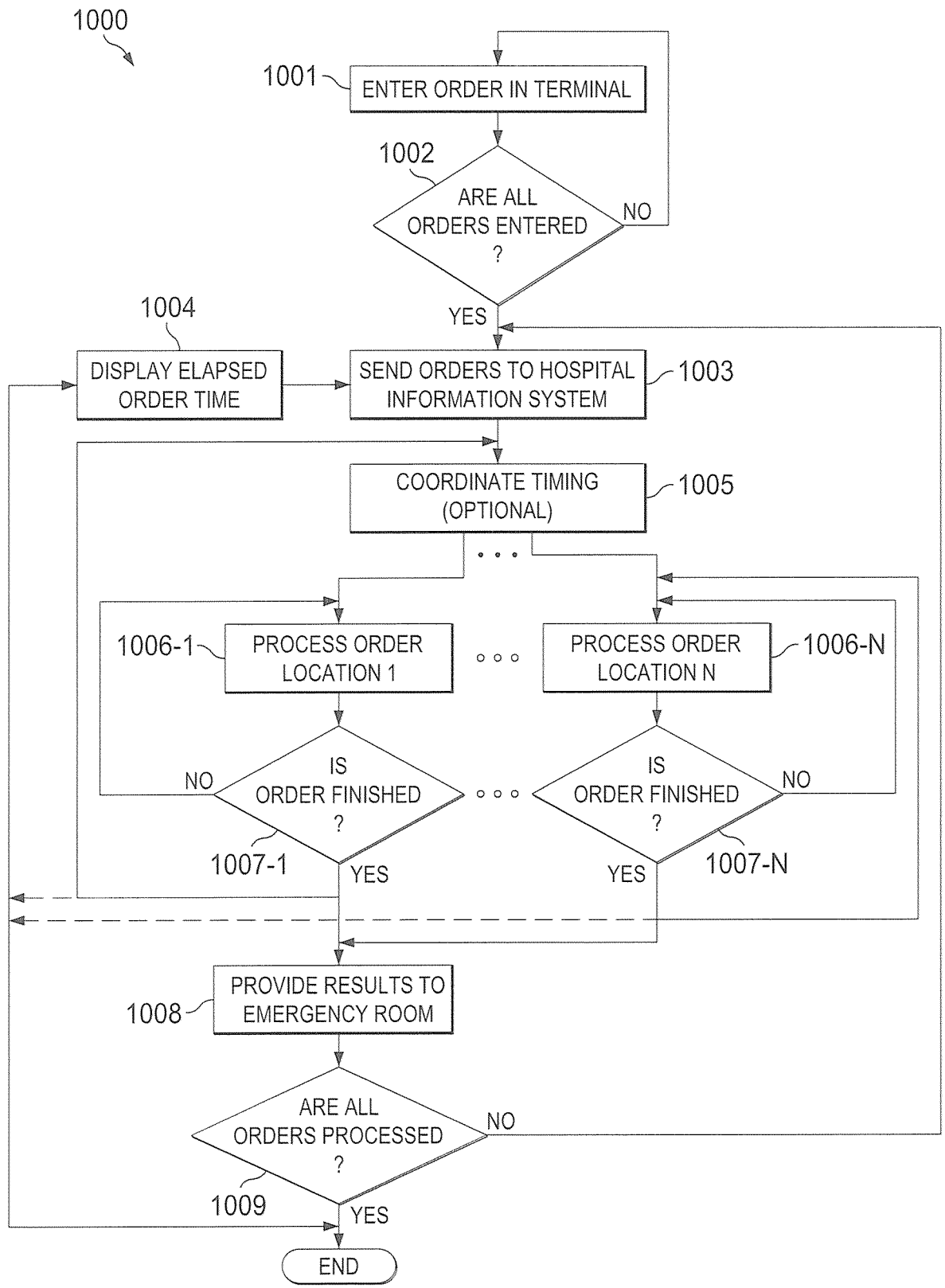
FIG. 10 shows one embodiment of a method of operation of the order entry procedure discussed herein.

FIG. 10 shows one embodiment of a method, such as method 10, of operation of the order entry system discussed herein. Process 1001 allows the physician, or authorized care giver, to perform patient examinations and to issue patient related orders. In the context of this application, the phase care giver assumes that the person has authority to issues such orders.

Process 1002 determines if al the desired orders have been selected. In one embodiment, as discussed above, the care giver can enter as many orders, even pertaining to different medical conditions as desired in one batch. Thus, when the care giver has determined that all orders have been selected, the care giver enables the subsequent processing of the selected orders as discussed above. The orders are transmitted to the hospital central system from the order entry system and process 1003 then sends the various orders to the proper department or other personnel as is appropriate for each order. Data is sent to the elapsed time display via process 1004.

Process 1005, if desired, coordinates the sequential timing among all of the orders and processes 1006-1 to 1006-N process each order in the respective departments. Processes 1007-1 to 1007-N determine when each order is completed. When complete, process 1008 provides the results both to the database and to the emergency room. Process 1009, on a patient by patient basis determines when all orders are completed. When all of the orders are completed the elapsed time display for the patient is updated. In situations where each order is tracked on the display, the elapsed timer is updated by process 1007-1 to 1007-N on an order by order basis.

Figure 11A:
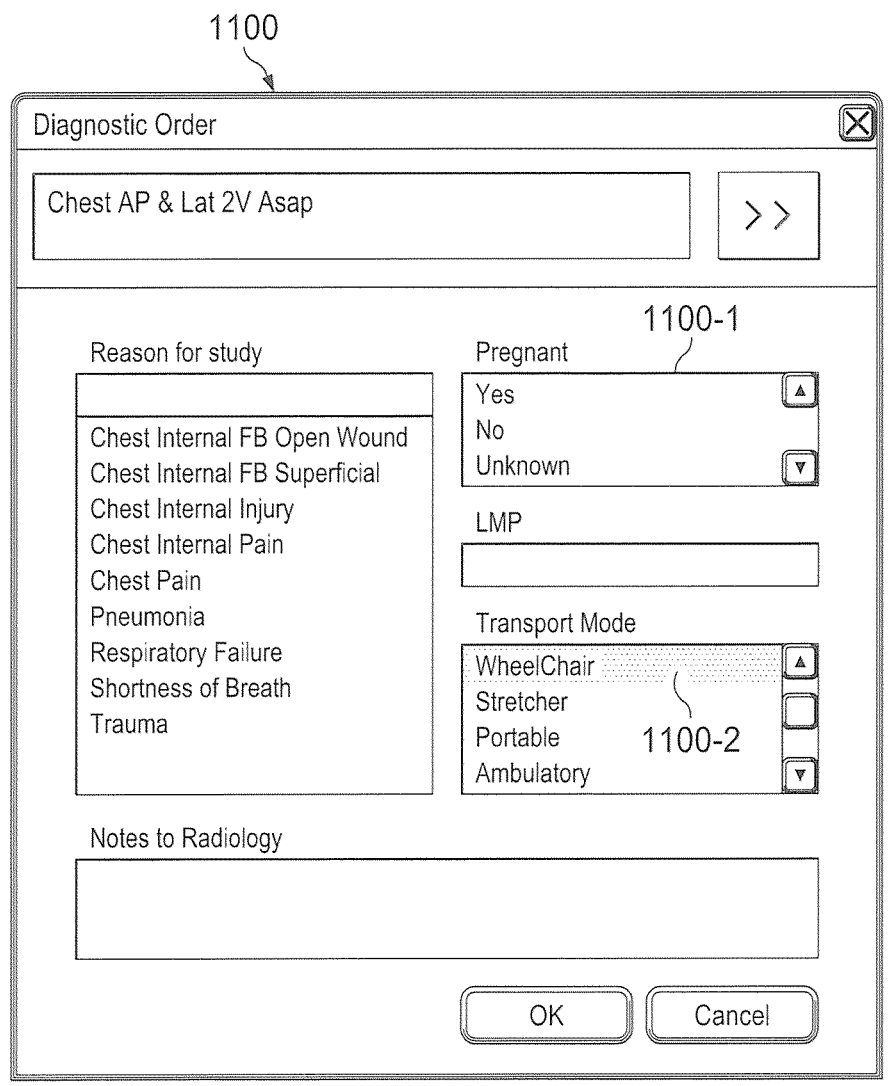
FIGS. 11A, 11B and 11C show embodiments of orders for various conditions.
Figure 11B:
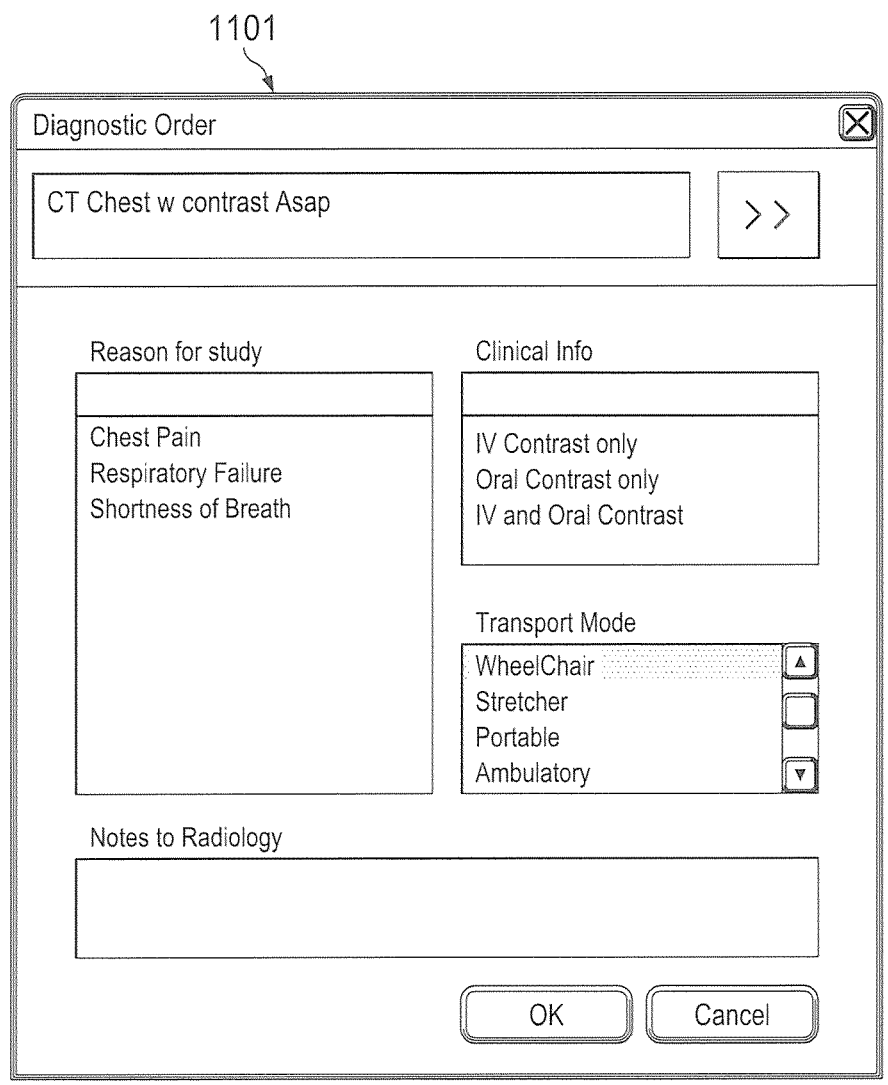
Figure 11C:
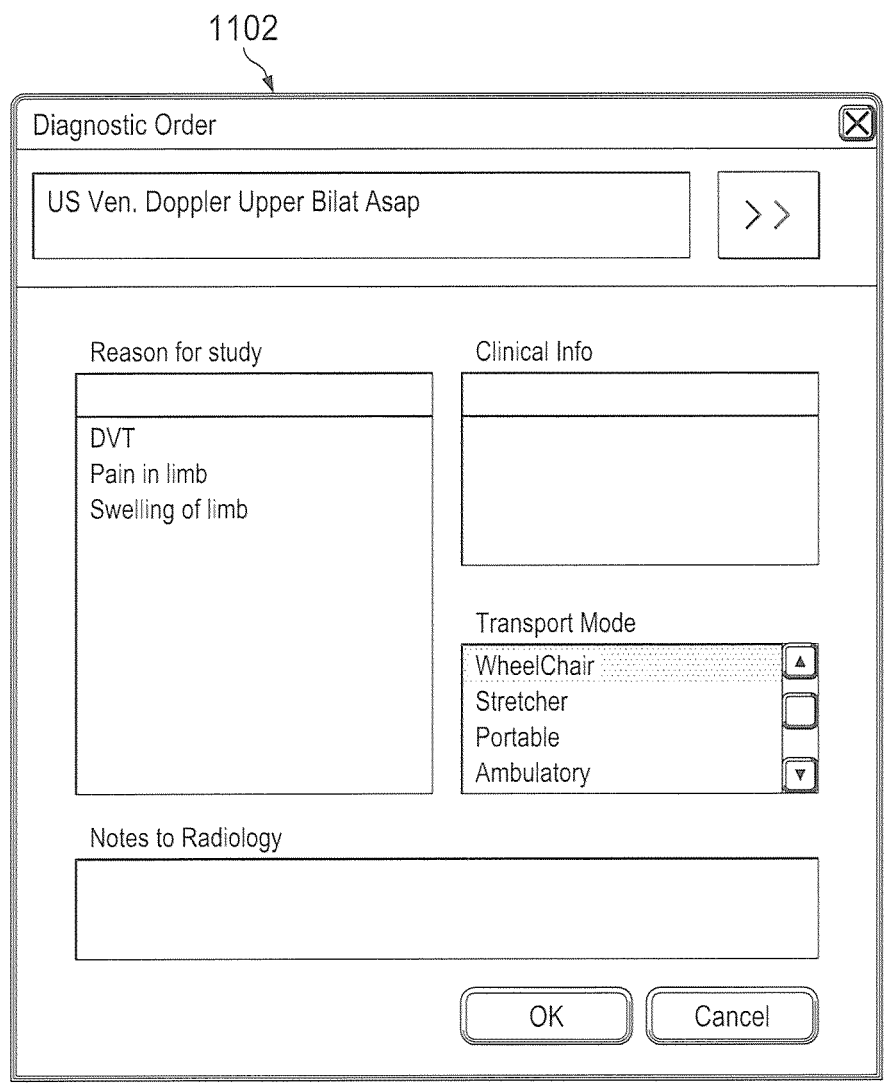

FIGS. 11A, 11B and 11C show embodiments of orders for various conditions. FIG. 11A shows order 1100 which is a diagnostic order for a Chest AP and Lat 2V. The physician can circle which symptom(s) he/she is concerned with and also can give other pertinent information in areas 1100-1 and 1100-2.

FIG. 11B shows an example of order 1101 for CT Chest with Contrast. FIG. 11C shows an example of order 1102 for US Ven. Doppler Upper Bilat. Note that each of these orders only contains information pertinent to the particular action being requested (ordered) and this allows the attending physician to easily provide the proper information.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A machine controlled method for medical practice order entry, said method comprising:

executing, by a processing device, a computerized medical order entry program which is configured to populate an order selection display to accept medical orders from a user;

displaying, under control of said processing device, a single page display containing a first section which lists a plurality of selectable medical conditions;

displaying in the single page display, under control of said processing device, a plurality of columns of possible orders, each column in said plurality of columns displayed concurrently with each other;

associating each column of said plurality of columns with a different category of a plurality of categories of medical order types;

receiving a selection, from said user, of a medical condition of the plurality of selectable medical conditions, wherein the selection by said user is made using an input device of said machine;

identifying a plurality of pre-defined order sets based on the selected medical condition, wherein each pre-defined order set of the plurality of pre-defined order sets comprises pre-defined individually selectable orders that are pre-defined to be directly related to said selected medical condition;

determining, for each pre-defined order set of the plurality of pre-defined order sets, with which category of a plurality of categories of medical order types each pre-defined order set is associated;

populating each column of the plurality of columns on said single page display with respective pre-defined order sets based on the associated category of medical order types, wherein populating each column of the plurality of columns on said single page display comprises:

dynamically arranging selectable elements within respective columns of the plurality of columns based on a selected category of medical order types, wherein each selectable element of the selectable elements corresponds to a pre-defined individually selectable order of said pre-defined individually selectable orders, and wherein at least a portion of said selectable elements are arranged in pre-determined positions with respective columns of the plurality of columns;

receiving a selection, by said user, of multiple ones of said pre-defined individually selectable orders, at least one of said multiple ones of said predefined individually selectable orders being further modifiable by said user upon being selected by said user;

receiving information, from the user, modifying the at least one of said multiple ones of said predefined individually selectable orders;

updating the at least one of said multiple ones of said predefined individually selectable orders based on the received information;

providing to a centralized server, said selected multiple ones of said pre-defined individually selectable orders, wherein the centralized server is configured to:

record in a database said selected multiple ones of said pre-defined individually selectable orders;

generate a workflow based on said selected multiple ones of said pre-defined individually selectable orders;

send a first request to a first department ordering a first medical service be performed by the first department;

send a second request to a second department ordering a second medical service be performed by the second department;

track times associated with completion of each order; and update the single page display to indicate a status of each order based on an elapsed amount of time based on the tracking of times.

2. The method of claim 1 further comprising:

receiving, from said user, a selection of another medical condition;

after receiving said selection of said medical condition, and upon receiving said selection of said another medical condition, changing said respective pre-defined order sets populating each of said plurality of columns;

receiving a selection of said individually selectable orders in said pre-defined order sets displayed in response to the selection of the another medical condition for each said category; and distributing selected orders to pertinent departments which carry out the selected orders.

3. The method of claim 1 wherein sending said first request comprises:

issuing appropriate orders to individuals, said issuing occurring under control of another processing device, which is associated with said first department.

4. The method of claim 1 further comprising:

staging a timing of said order issuing in accordance with pre-established staging protocols.

5. The method of claim 1 wherein said dynamically arranging selectable elements in the single page display further comprises:

placing certain selectable elements corresponding to said individually selectable orders in the same position in columns of said plurality of columns for a plurality of said medical conditions.

6. The method of claim 1, wherein said first medical service is a diagnostic service, and the method further comprises:

receiving, from a processor performing said diagnostic service, results of said diagnostic service.

7. The method of claim 1, wherein said first medical service is an action performed by an individual, and the method further comprises:

receiving, from another processing device associated with the first department, results of said performance of said action.

8. A method of administering orders in an emergency medical environment having high volumes and limited time per patient initial evaluation, said method comprising:

entering orders corresponding to an initial evaluation of a patient into an automated order entry computing device, said entry computing device having a display for use by said care giver, said entering comprising:

selecting a patient presented medical condition from a displayed list of possible medical conditions using said order entry computing device;

displaying, in a single page of said display, a plurality of columns of possible orders, each column in said plurality of columns displayed concurrently with each other;

associating each column of said plurality of columns with a different category of a plurality of categories of medical order types;

identifying a plurality of pre-defined order sets based on the selected patient presented medical condition, wherein each pre-defined order set of the plurality of pre-defined order sets comprises individually selectable orders that are pre-defined to be directly related to said selected patient presented medical condition, said individually selectable orders in said pre-identified set of orders being modifiable by said care giver upon being selected by said care giver;

determining, for each pre-defined order set of the plurality of pre-defined order sets, with which category of a plurality of categories of medical order types each pre-defined order set is associated;

populating each column of said plurality of columns with respective pre-defined sets of orders based on the associated category of medical order types, wherein populating each column of said plurality of columns comprises:

dynamically arranging selectable elements within respective columns of said plurality of columns based on a selected category of medical order types, wherein each selectable element of the selectable elements corresponds to a pre-defined individually selectable order of said pre-defined individually selectable orders, and wherein at least a portion of said selectable elements are arranged in pre-determined positions with respective columns of the plurality of columns;

selecting, using said order entry computing device, appropriate orders from said individually selectable orders presented on said display in the plurality of columns using said selectable elements, wherein said plurality of columns, orders and listing of possible medical conditions are simultaneously displayed on a single page;

sending, said selected appropriate orders to a central processing device, wherein said central processing device performs the steps of:

mapping a first order of said selected appropriate orders to a first code specific for a first department and transmitting said first code to another processor designated to the first department; and mapping a second order of said selected appropriate orders to a second code specific for a second department and transmitting said second code to another processor designated to the second department;

tracking times associated with completion of each order; and updating the single page display to indicate a status of each order based on an elapsed amount of time based on the tracking of times.

9. The method of claim 8 wherein said entering further comprises:

selecting said individually selectable orders from said pre-defined order sets wherein certain of said individually selectable orders are arranged in the same position in said plurality of columns for a plurality of said conditions.

10. The method of claim 8 further comprising:

providing timing control for said individually selectable orders for proper sequencing of an execution of said individually selectable orders based on said tracking.

11. The method of claim 8 further comprising:

displaying for each patient a lapsed time since a particular order for said patient has been placed, wherein said lapsed is determined based on said tracking.

12. The method of claim 8 further comprising:

selecting a second patient presented medical condition from a displayed list of possible medical conditions using said order entry computing device; and upon receiving a selection of a patient presented medical condition, populating said plurality of columns corresponding to said different categories of medical orders with different pre-defined order sets of individually selectable orders which are identified as being associated with the selected second patient presented medical condition.

13. The method of claim 8, wherein said first code is associated with a first medical service to be performed by the first department, said first medical service being a diagnostic service, and wherein said central processing device performs the further steps of:

receiving, from a processor performing said diagnostic service, results of said diagnostic service.

14. The method of claim 8, wherein said first code is associated with a first medical service to be performed by the first department, said first medical service being an action performed by an individual, and wherein said central processing device performs the further steps of:

receiving, from another processing device associated with the first department, results of said performance of said action.

* * * * *